(12) United States Patent
Erdman et al.

(10) Patent No.: US 8,128,609 B2
(45) Date of Patent: Mar. 6, 2012

(54) ABSORBENT ARTICLE WITH IMPROVED SIDE SEAMS

(75) Inventors: Edward P Erdman, West Chester, PA (US); Nicole DiVittore, West Chester, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 0 days.

(21) Appl. No.: 11/973,506

(22) Filed: Oct. 9, 2007

(65) Prior Publication Data

US 2008/0058750 A1    Mar. 6, 2008

Related U.S. Application Data

(62) Division of application No. 11/200,832, filed on Aug. 10, 2005, now abandoned.

(51) Int. Cl.
*A61F 13/15* (2006.01)
*A61F 13/20* (2006.01)

(52) U.S. Cl. .............. 604/385.29; 604/385.24

(58) Field of Classification Search ............. 604/385.01, 604/385.24, 385.29, 385.3, 385.22, 386, 604/394; 156/161, 179, 436
See application file for complete search history.

(56) References Cited

U.S. PATENT DOCUMENTS

2003/0089447 A1*  5/2003  Molee et al. ................. 156/161
* cited by examiner

*Primary Examiner* — Michele M Kidwell
(74) *Attorney, Agent, or Firm* — Amster, Rothstein & Ebenstein LLP (57) ABSTRACT

An absorbent article is provided that includes a top sheet and a back sheet joined to form side seam regions. An absorbent core is disposed between the top sheet and the back sheet; and laterally oriented elastics are disposed between the top sheet and the back sheet. The elastics include a first elastic region disposed adjacent to the front end and a second elastic region disposed adjacent the first elastic region. The second elastic region includes one or more elastic elements that extend between the side seam regions. The elastic elements have internal cuts adjacent the side seams in a configuration that relieves elastic tension adjacent the side seams regions.

9 Claims, 7 Drawing Sheets

ABSORBENT ARTICLE WITH IMPROVED SIDE SEAMS

This application is a divisional of U.S. patent application Ser. No. 11/200,832, filed Aug. 10, 2005.

BACKGROUND

1. Technical Field

The present disclosure generally relates to absorbent articles, and more particularly to an absorbent article having a side seam structure including severed elastics disposed in a configuration that is softer and more aesthetically pleasing to the wearer for improving fit, while being low cost and easily manufactured.

2. Description of the Related Art

Absorbent articles such as, for example, disposable diapers, adult incontinent pads, sanitary napkins, pantiliners, incontinent garments and the like are generally worn, in cooperation with garments and disposed against a body surface by infants or adult incontinent individuals. The absorbent article is employed to collect and absorb body fluid discharge, such as, for example, blood, menses, urine, aqueous body fluids, mucus, cellular debris and other forms of body discharge. For example, the absorbent article may be disposed between the legs of an individual adjacent a crotch area. The absorbent article is positioned with a garment and drawn into engagement with a body surface of the crotch area to collect body discharge.

As is known, absorbent articles typically include a fluid permeable coverstock for engaging the body surface, a fluid impermeable backsheet and an absorbent core supported therebetween. The backsheet serves as a moisture barrier to prevent fluid leakage to the garment. The absorbent core usually includes a liquid retention material that faces the body surface. The absorbent core can include, for example, loosely formed cellulosic fibers, such as, for example, wood pulp, rayon, or cotton for acquiring and storing body discharge. The absorbent core may also include tissue wrapping or wadding, and/or super absorbent polymer.

Some absorbent article designs typically incorporate elastic elements in the waist, stomach, and leg areas for improving the fit, aesthetics and leakage resistance. The waist and stomach elastic elements increase the flexibility of the absorbent article, allowing the same article to accommodate a greater range of body sizes. In addition, they make the article more form-fitting for the wearer. The topsheet and backsheet are joined to support the components of the absorbent article.

Infants, toddlers, and other incontinent individuals wear disposable absorbent articles such as diapers and training pants, which include "pull-on" or "pant-type" garments having fixed sides, single-use diaper garments including front and back portions joined, usually by an adhesive, when the diaper is initially donned, and hybrid garments which are donned like a diaper garment but are designed to be removed and replaced like a pant-type garment.

Typically, the elasticized elements disposed adjacent the side seams cause bunching at the side seam. This disadvantageous bunching of the garment about the wearer results in many drawbacks such as discomfort and leakage.

It would therefore be desirable to overcome the disadvantages and drawbacks of the prior art by providing an absorbent article having a side seam structure including severed elastics disposed in a configuration that is softer and more aesthetically pleasing to the wearer for improving fit. Such an absorbent article desirably prevents leakage. It is contemplated that the absorbent article is low cost and easy and efficient to manufacture.

SUMMARY

Accordingly, an absorbent article having a side seam structure, including severed elastics adjacent to the side seams, disposed in a configuration that is softer and more aesthetically pleasing to the wearer for improving fit is provided. Such an absorbent article desirably prevents leakage. The absorbent article is low cost and easy and efficient to manufacture. Objects and advantages of the present disclosure are set forth in part herein and in part will be obvious therefrom, or may be learned by practice of the present disclosure that is realized and attained by the instrumentalities and combinations pointed out in the appended claims for the devices and methods of the present disclosure consisting of its constituent parts, constructions, arrangements, combinations, steps and improvements herein shown and described.

In one particular embodiment, in accordance with the principles of the present disclosure, an absorbent article is provided that defines a longitudinal axis, and a front end and a back end disposed along the longitudinal axis, comprising (i) a garment-facing surface comprising a fluid-impermeable back sheet, (ii) a body-facing surface comprising a fluid-permeable top sheet, the garment-facing surface and the body-facing surface being joined to form side seam regions; (iii) at least one absorbent core disposed between the garment-facing surface and the body-facing surface; and (iv) laterally oriented elastics, relative to the longitudinal axis, being disposed between the garment-facing surface and the body-facing surface, the elastics including a first elastic region disposed adjacent to the ends of the article (i.e., the front end and the back end) and a second elastic region disposed adjacent the first elastic region, the second elastic region including one or more elastic elements that extend between the side seam regions, wherein the elastic elements have internal cuts adjacent the side seam regions in a configuration that relieves elastic tension in the side seam regions.

The front end and the back end of the absorbent article are each defined by two laterally-disposed side panel regions and a medially-disposed body facing region and the internal cuts are disposed in the side panel regions. Preferably, the internal cuts are disposed in the lateral side panel region. It is also contemplated that the second elastic region has internal cuts in the body facing regions of the front and back ends.

In alternate configurations, the first elastic region comprises one or more elastic elements and at least one of the elastic elements has one or more internal cuts adjacent to the side seams in a configuration that relieves elastic tension. Preferably, these cuts are in the lateral side panel region but not in the medial side panel region. It is also contemplated that one or more of the elastic elements has internal cuts in the body facing regions.

It is contemplated that the elastic elements of the first elastic region and/or the second elastic region are disposed within a laminate structure. The elastic elements of the first elastic region and/or the second elastic region may be present within the same laminate structure or within different laminate structures.

In another embodiment, the present disclosure provides an absorbent article having a longitudinal axis, a front region and a back region disposed along the longitudinal axis, wherein the front and back regions each being characterized by a medially-disposed body facing region and two laterally-disposed side panels, the side panels being characterized as having a medial region and a distal region, comprising: (i) a fluid-impermeable back sheet, (ii) a fluid-permeable top sheet, and the back sheet being joined to form side seam regions; (iii) at least one absorbent core disposed between the top sheet and the back sheet; and (iv) a waistband having one or more elastic members disposed perpendicular to the longitudinal axis running substantially the entire width of each of the front region and the back region, and (v) a tummy band disposed adjacent to the waistband having one or more elastic members disposed perpendicular to the longitudinal axis and running substantially the entire width of each of the front region and the back region, wherein the elastic members have one or more internal cuts adjacent the side seam regions in a configuration that relieves elastic tension in the side seam regions. Preferably, the internal cuts are in the distal regions of the side panels. It is also contemplated that at least one of the elastic members of the first elastic region and/or at least one of the elastic members of the second elastic region has internal cuts in the body facing region.

In another embodiment, this disclosure provides a method for manufacturing an absorbent article comprising: (i) providing an elastic member, a top sheet, a back sheet and an adhesive; (ii) applying the adhesive to at least one side of the elastic member; (iii) assembling the absorbent article having a laminate structure wherein the adhesive is disposed between the elastic member and the top sheet; the top sheet and the bottom sheet being joined (iv) making internal cuts in the laminate structure adjacent the area that will include the side seams. Preferably, the elastic member is under elastic tension during assembly of the laminate structure.

The adhesive may be applied continuously but is, preferably, applied discontinuously such that the elastic member is characterized as having adhesive-containing regions and non-adhesive-containing regions. In the most preferred embodiment, the internal cuts are made in non-adhesive-containing regions of said elastic member. These internal cuts may be made using a heated knife roller.

Adhesive may be further disposed between the elastic member and the side seams may be joined along longitudinal edge of the absorbent article.

In any of the foregoing embodiments, the absorbent core may consist of wood pulp, cellulose wadding, cotton fibers, absorbent foams, sponges, superabsorbent polymers (e.g., hydrogels), absorbent gelling materials, or combinations thereof.

The present disclosure also provides a method for manufacturing a laminate structure comprising: (i) providing an elastic member, an upper sheet, a lower sheet, and an adhesive; (ii) discontinuously applying the adhesive to at least one side of the elastic member such that said elastic member is characterized as having adhesive-containing regions and non-adhesive-containing regions; (iii) assembling the absorbent article having a laminate structure wherein the elastic member is disposed between the upper sheet and the lower sheet, the upper sheet and the lower sheet being joined to form a laminate structure, and wherein the elastic member is under elastic tension during assembly; (iv) making internal cuts in the laminate structure, wherein the internal cuts are made in the non-adhesive-containing regions of the elastic member such that the elastic tension of the elastic member is relieved in the area of the internal cuts.

In one embodiment, adhesive is applied to both sides of the elastic member. In another embodiment, the internal cuts are made using a heated knife roller. Preferably, the cuts made in the upper sheet and/or the lower sheet are heat-sealed by the knife roller.

It is contemplated that the laminate structure contain multiple elastic members. In one embodiment, the internal cuts are made in each elastic member of the laminate structure. In another embodiment, the internal cuts are made in fewer than all elastic members of the laminate structure. It is further contemplated that the laminate structure will be further cut into unitary lengths. In preferred embodiments, at least some of the internal cuts are adjacent to the ends of the unitary lengths.

BRIEF DESCRIPTION OF THE DRAWINGS

The objects and features of the present disclosure are set forth with particularity in the appended claims. The present disclosure, as to its organization and manner of operation, together with further objectives and advantages may be understood by reference to the following description, taken in connection with the accompanying drawings, in which:

DETAILED DESCRIPTION OF THE EXEMPLARY EMBODIMENTS

The exemplary embodiments of the absorbent article and methods of use disclosed are discussed in terms of fluid absorbent articles, and more particularly, in terms of an absorbent article having a side seam region including severed elastics disposed in a configuration that is softer and more aesthetically pleasing to the wearer for improving fit, while being low cost and easily manufactured. The presently disclosed absorbent article is contemplated to be employed with, for example, training pants, adult incontinent products, disposable diapers, and other incontinent articles. It is contemplated that by pre-cutting the elastic members of a second elastic region alone or the elastic members of both the second elastic region and the first elastic region in the distal region of the side panels of an absorbent article, bunching and leakage is prevented at the side seam region when the article is worn.

In the discussion that follows, the term "body-facing surface" refers to a portion of a structure that is oriented towards a body surface, and the "garment-facing surface" refers to a portion of the structure that is oriented towards a garment and is typically opposing the body-facing surface and may be referred to as such. As used herein, the term "body surface" refers to a portion of an individual's body that the absorbent article is disposed with for collecting and absorbing fluid discharge from the individual. As used herein, the term "absorbent article," or "absorbent garment" refers to garments that absorb and contain body waste, and more specifically, refers to garments that are placed against or in proximity to the body of the wearer to absorb and contain the various body discharges and wastes. As used herein, the term "side seam region" refers to the lateral region of the absorbent article that functionally forms and supports the side seam. This region includes the side seam itself in addition to the distal region of the lateral region of the absorbent article.

A non-exhaustive list of examples of absorbent articles includes training pants, diapers, diaper covers, disposable diapers, feminine hygiene products and adult incontinence products. The term absorbent articles includes all variations of absorbent garments, including disposable absorbent garments that are intended to be discarded or partially discarded after a single use and unitary disposable absorbent garments that have essentially a single structure. As used herein, the term "training pants" refers to an absorbent article generally worn by children about the lower torso. The absorbent article may be disposable or partially discarded after a single use. The absorbent article can be a unitary structure or include replaceable inserts or interchangeable parts.

Absorbent articles and diapers may have a number of different constructions. In each of these constructions it is generally the case that an absorbent core is disposed between a liquid pervious, body-facing top sheet and a liquid impervious, exterior facing back sheet. In some cases, one or both of the top sheet and back sheet may be shaped to form a pant-like article, such as a training pant. In other cases, the top sheet, back sheet and absorbent core may be formed as a discrete assembly that is placed on a main chassis layer and the chassis layer is shaped to form a pant-like absorbent article. The absorbent article may be provided to the consumer in the fully assembled pant-like shape or may be partially pant-like and require the consumer to take the final steps necessary to form the final pant-like shape. Training pants are typically fully formed and applied by pulling the absorbent article over a child's legs. For a diaper application, an open article is provided and wrapped about a child's waist, such as by manually fastening one or more fasteners or fastener tabs.

The following discussion includes a description of the disposable absorbent article in accordance with the present disclosure. Reference will now be made in detail to the exemplary embodiments of the disclosure, which are illustrated in the accompanying figures. Like components are designated by like reference numerals throughout the several views.

Figure 1A:
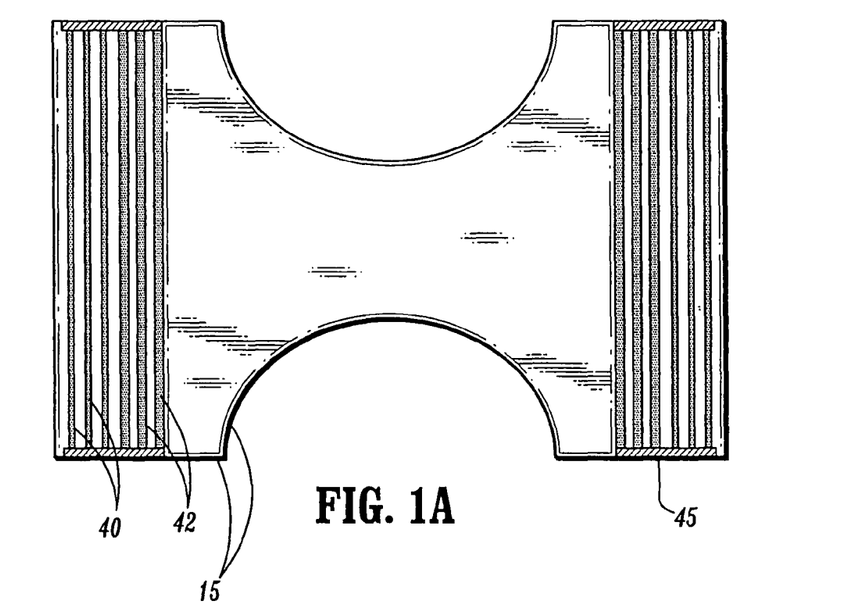
FIG. 1A is a plan view of an absorbent article having continuous (uncut) elastic members.
Figure 1B:
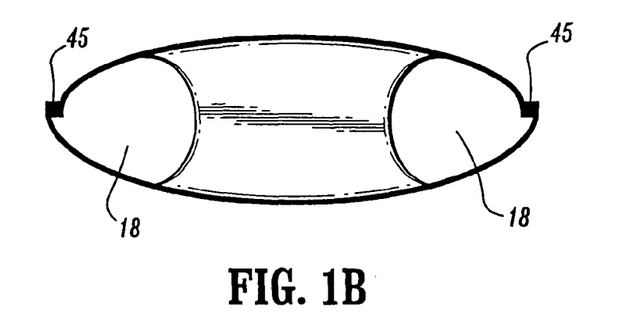
FIG. 1B is a top view of the absorbent article, shown in FIG. 1A, in an assembled configuration.
Figure 1C:
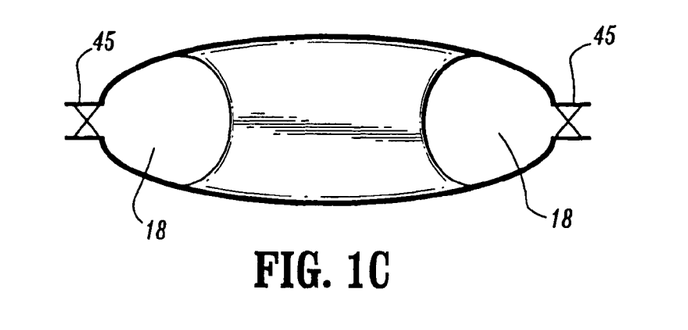
FIG. 1C is a top view of the absorbent article, shown in FIG. 1A, in an alternate embodiment of the assembled configuration.

As shown in FIG. 1A, an absorbent article is shown having first 30 and second 32 elastic regions (see FIG. 2) comprised of continuous elastic members 40 and 42, respectively, that are under elastic tension. FIG. 1B shows a top-view of a diaper-style absorbent article in its "donned" configuration in which the side panels have been fastened as if around a person's waist, forming the leg openings 18. In this configuration, the side seam region described in more detail below, are joined to form side seams 45 in an overlap configuration. The overlap configuration includes joining the outer surface of the front or back end to the inner surface of respective back or front end. In an alternate embodiment, as shown in FIG. 1C, the side seam regions are joined in a cross or transverse configuration to form side seams 45. The transverse configuration includes joining the inner surfaces of the front and back ends. It is envisioned that transverse configuration may include joining the outer surfaces of the front and back ends. It is envisioned that side seams 45 may be joined in various configurations.

Figure 2:
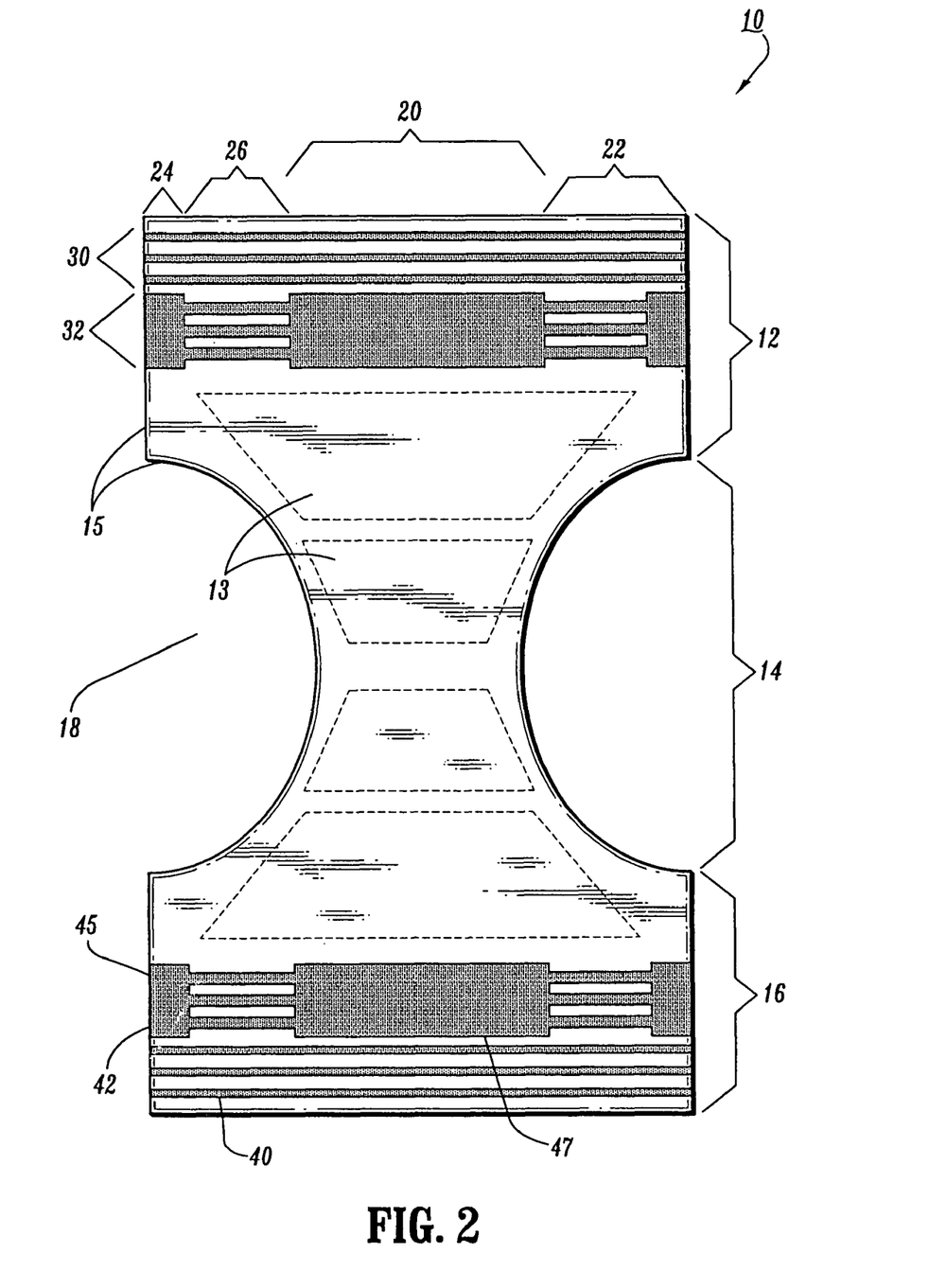
FIG. 2 is a plan view of an absorbent article having the elastic members of the second elastic region internally cut in distal regions of side panels.

In an alternate embodiment, FIG. 2 illustrates an absorbent article 10 constructed in accordance with the principals of this disclosure. Absorbent article 10 has a longitudinal axis and extends from a front end corresponding to a front region 12, a crotch region 14, to back end corresponding to a back region 16 that are disposed along that axis. The crotch region 14 is further characterized as having laterally disposed leg openings 18. The garment-facing surface such as, for example, a fluid impermeable back sheet, and the body-facing surface, such as, for example, a fluid permeable top sheet, are joined to form the side seam regions, which include side panels 22 of absorbent article 10 and side seams 15. The garment facing surface and the body facing surface support the absorbent core(s) 13. Although the front region 12 and the back region 16 are illustrated as being symmetrical in shape, symmetry is not necessary.

Each of the front region 12 and back region 16 are further characterized as having a medially-disposed body facing region 20 and two laterally-disposed side panels 22. Each laterally-disposed side panel 22 is further characterized as having a distal region 24 and a medial region 26. It is contemplated that the side seam regions include side panels 22 and the side seams 15, which are supported by the junction of the garment-facing surface and the body-facing surface, along with at least the distal region of the side panel 24. Further, the front region 12 and back region 16 each have a first elastic region 30 and a second elastic region 32. It is contemplated that first elastic region 30 may be configured as a waistband. It is further contemplated that second elastic region 32 may be configured as a tummy band.

The first elastic region 30 has at least one elastic member 40 running substantially perpendicular to the longitudinal axis and spanning substantially the entire width of the region. The first elastic region elastic member 40 may be contained within a laminate structure 100 (see FIGS. 4-6) or may be affixed directly to the garment-facing surface, body-facing surface, and/or absorbent core. It is understood, unless specifically excluded, that a reference to the "first elastic region elastic member 40," or more simple the "elastic member 40" is also meant to refer to the comparable region of a laminate structure 100 which is described in detail below. The elastic member(s) 40 may be held in place by use of an adhesive which may be continuous or discontinuous along the length of the elastic member 40 or the elastic member 40 may be held in place by fused ends between the garment-facing surface and the body-facing surface during assembly of the absorbent article 10. In cases where an adhesive is used, the elastic member 40 may be adhered to the garment-facing surface, the body-facing surface, and/or the absorbent core 13.

The second elastic region 32 is disposed, adjacent and medially to the first elastic region 30, and has at least one elastic member 42 (also referred to as the "second elastic region elastic member 42") running substantially perpendicular to the longitudinal axis and spanning substantially the entire width of the region. The second elastic region elastic member 42 may be contained within a laminate structure 100 (see FIGS. 4-6) or may be affixed directly to the garment-facing surface, body-facing surface, and/or absorbent core. It is understood, unless specifically excluded, that a reference to the "second elastic region elastic member 42" is also meant to refer to the comparable region of a laminate structure 100 which is described in detail below. During manufacture, the second elastic region elastic member(s) 42 may be held in place by sealing the ends between the top sheet and the back sheet. The second elastic region 32 is further characterized as having discontinuous elastic members 45 adjacent side seams 15 in the distal region of the side panels 24 and may optionally have discontinuous elastic members 47 in the body facing region 20 of the front and back panels 12 and 16. The second elastic region elastic members 42 may be rendered discontinuous by cutting following assembly of the absorbent article 10 or they may be precut following the assembly of the laminate structure 100 prior to final assembly of the absorbent article 10 (see FIGS. 4-6). Second elastic region elastic member 42 cutting may be done in accordance with the principles of this disclosure (see FIGS. 5 and 6; i.e., using a knife roller 172 that may, preferably, be heated to seal the cuts made in the back sheet and/or top sheet) or by any convenient method.

The discontinuous elastic members 45 relieve the elastic tension of the second elastic region in the side panel side seam region when the article is donned. This cutting of the second elastic region elastic members 42 to render them discontinuous 45 reduces or eliminates side seam bunching when the article is donned. The discontinuous elastic members 47 also serve to reduce or eliminate bunching in the front 12 and back 16 panels and enhance wearer comfort. Preferably, the discontinuous elastic members 45 and 47 are not adhered to the garment-facing surface and/or the body-facing surface and are cut in sufficiently small pieces to relieve elastic tension. It is contemplated that the discontinuous elastic members 45, 47 may have various dimensions, such as, for example, less than 0.5", less than 0.25", or less than 0.10". The elastic member(s) 42 in the medial region of the side panels 26 retain elastic tension and may be contained within a laminate structure 100 which is assembled into the absorbent article 10 or they may be adhered directly to the garment-facing surface, the body-facing surface, and/or the absorbent core. Accordingly, it is necessary to discontinuously apply an adhesive to the tummy band elastic member(s) 42 prior to cutting such that the adhesive is only present in the medial region of the side panels 26. Optionally, adhesive may be applied continuously or discontinuously to the body facing region 20 of the tummy band elastic member(s) 42, whether or not the tummy band elastic member(s) 42 are contained within a laminate structure 100.

Figure 3:
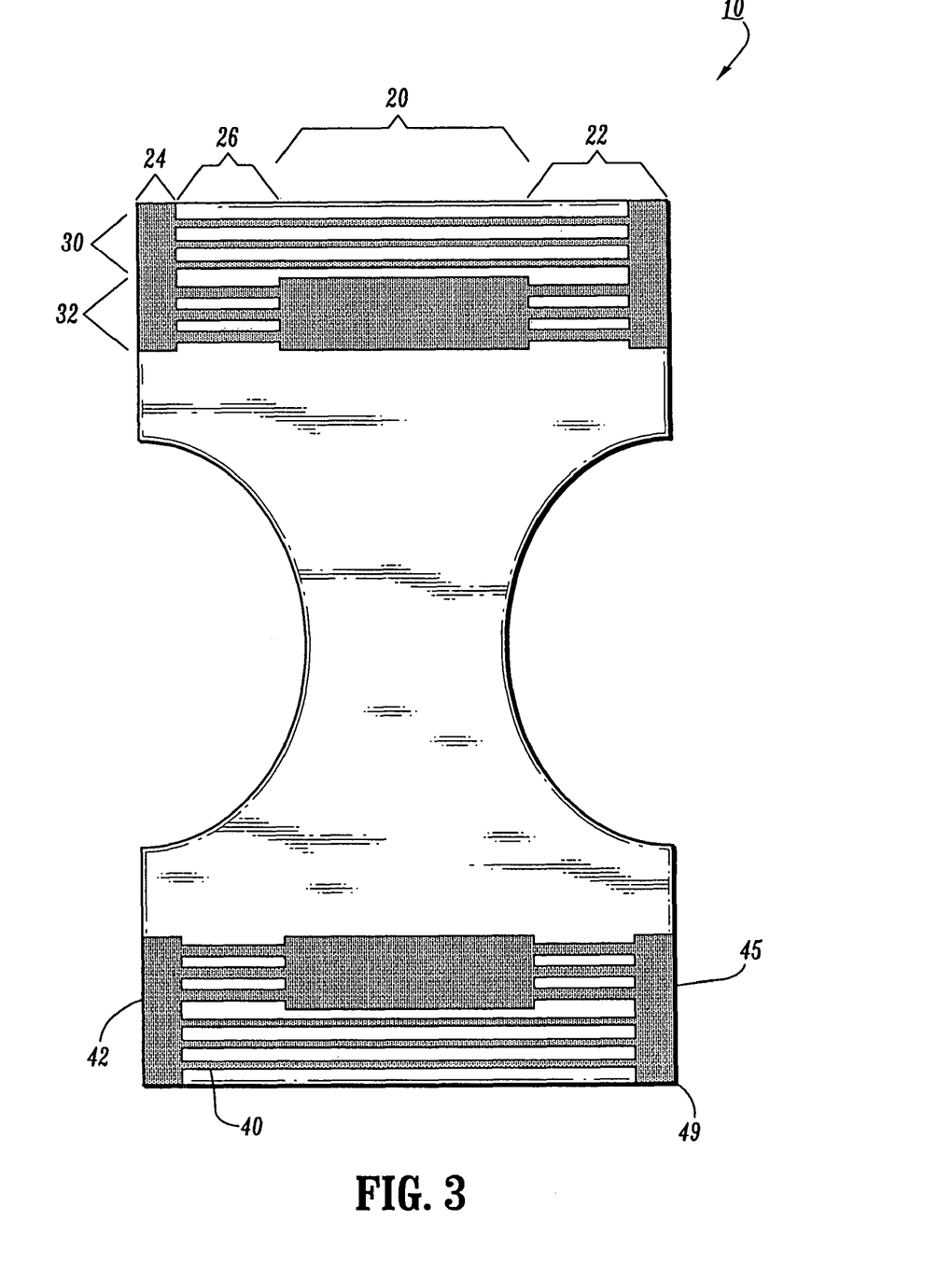
FIG. 3 is a plan view of an absorbent article having the elastic members of both the first and the second elastic regions internally cut in the distal regions of the side panels.

FIG. 3 illustrates an alternate embodiment of the absorbent article 10. This embodiment is similar to the one disclosed in FIG. 2 except that the first elastic region adjacent side seams 15 and elastic members 40 are discontinuous 49 by cutting to relieve elastic tension in the distal region of the side panels 24. As in FIG. 2, the waistband elastic members 40 may be bonded between the top sheet and the back sheet during assembly of the absorbent article 10. The cutting of the elastic members 40 is typically performed following assembly. The uncut portions of the waistband elastic members 40 in the medial region 26 and the body facing region 20 of each of the front 12 and back 16 regions must be adhered to the back sheet, the top sheet, and/or the absorbent core 13. This cutting of the waistband elastic members 42 to render them discontinuous 49 in the distal region 24 further reduces or eliminates side seam bunching when the article is donned.

In preferred embodiments, the second elastic region elastic members 42 and the first elastic region elastic members 40 are contained in a laminate structure 100. It is contemplated that the second elastic region elastic members 42 and, if desired, the first elastic region elastic members 32 are pre-cut during the manufacture of the laminate structure 100 but prior to the final assembly of the absorbent article 10. The laminated structure 100, containing both the continuous elastic members and the discontinuous (cut) elastic members, is assembled into the final absorbent article. The laminated structure 100 may be held in place by fusing the ends between the garment-facing surface and body-facing surface during final assembly, it may be held in place using an adhesive, or both. The second elastic region 32 and the first elastic region 30 may be contained within the same laminate structure 100 or separate laminate structures 100.

Figure 4:
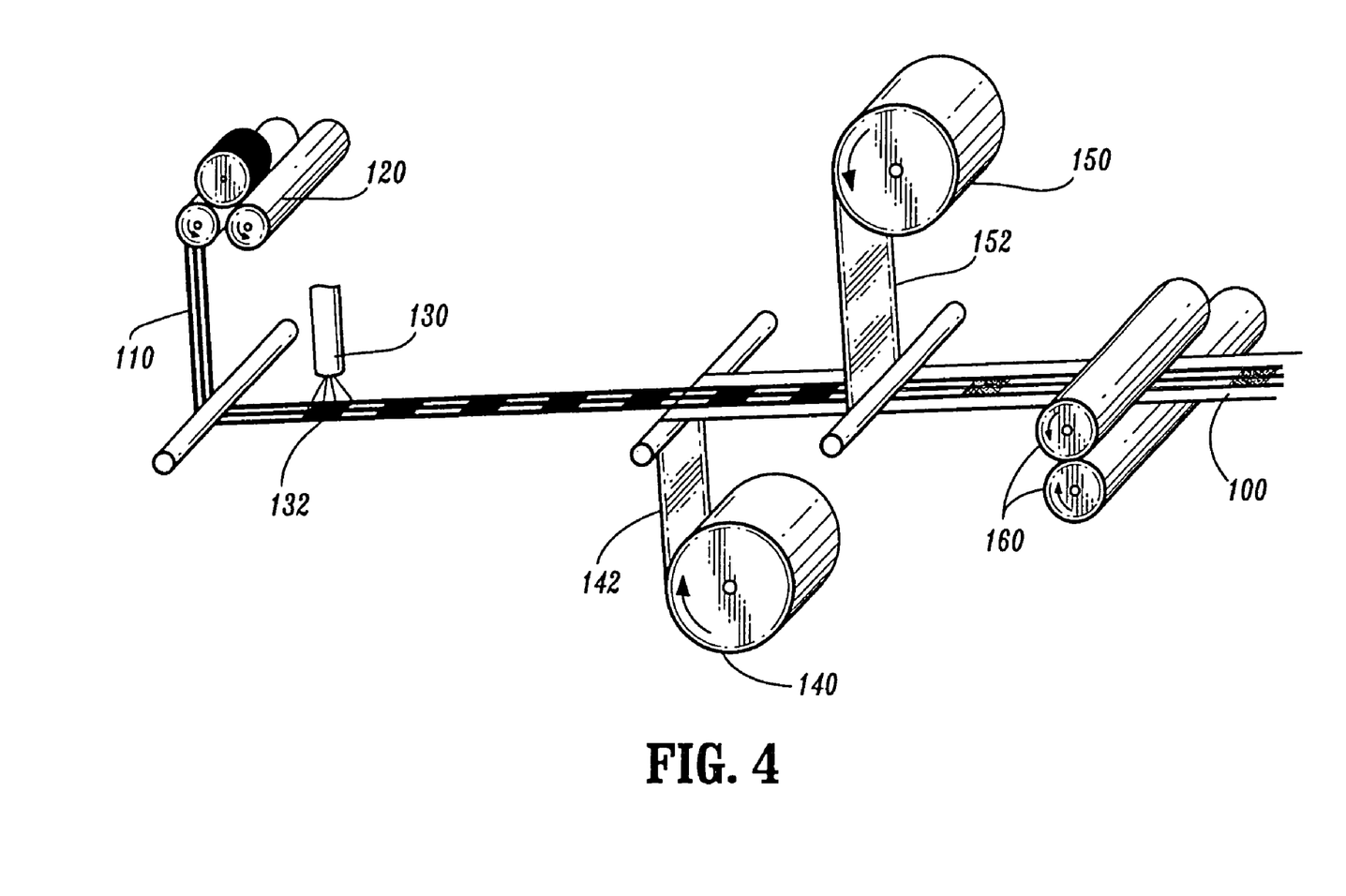
FIG. 4 is a schematic diagram of a manufacturing method for absorbent articles containing elastic members useful as first elastic regions and/or second elastic regions.

FIG. 4 is a schematic diagram demonstrating a method for manufacturing a laminate structure 100 suitable for use as a second elastic region 32, a first elastic region 30, or a combination first and second elastic regions in accordance with this disclosure. The elastic members 110 which may be used as the first elastic region elastic members 40 or the second elastic region elastic members 42 or both are wound on a roller apparatus 120. Adhesive 132 is applied by an adhesive applicator 130 in the desired discontinuous pattern, which depends upon the final desired configuration of the elastic members 110 in the absorbent article 10. These discontinuous patterns may vary based on whether the laminate structure 100 will be used as a first elastic region 30 or a second elastic region 32, or both, and whether the elastic members will be precut in the distal region of the side panels 24 alone or also include precuts in the body facing regions 20. Adhesive 132 may be applied to the top, lower, or both sides of the elastic members 110. A lower sheet 142 is applied to the lower of the elastic members 110 from a lower sheet roll stock 140. An upper sheet 152 is applied to the top of the elastic members 110 from an upper sheet roll stock 150. Although FIG. 3 illustrates the application of the lower sheet 142 prior to the application of the upper sheet 152, the order is unimportant to the configuration of the final laminate 100. Typically, although not necessarily, the upper sheet 152 and the lower sheet 142 are wider than the width of the elastic members 110. In preferred embodiments, the upper sheet 152 is joined at its edges to the lower sheet 142 to enclose the elastic members.

Next, the laminate 100 is run through compression rollers 160. The compression rollers 160 rotate at the same speed as the top sheet roll stock 150 and the lower sheet roll stock 140 is unwound which is, preferably, at a speed greater than the elastic 110 is unwound from the elastic roller apparatus 120. This has the effect of creating elastic tension within the final laminate 100 as it leaves the compression rollers 160.

Figure 5:
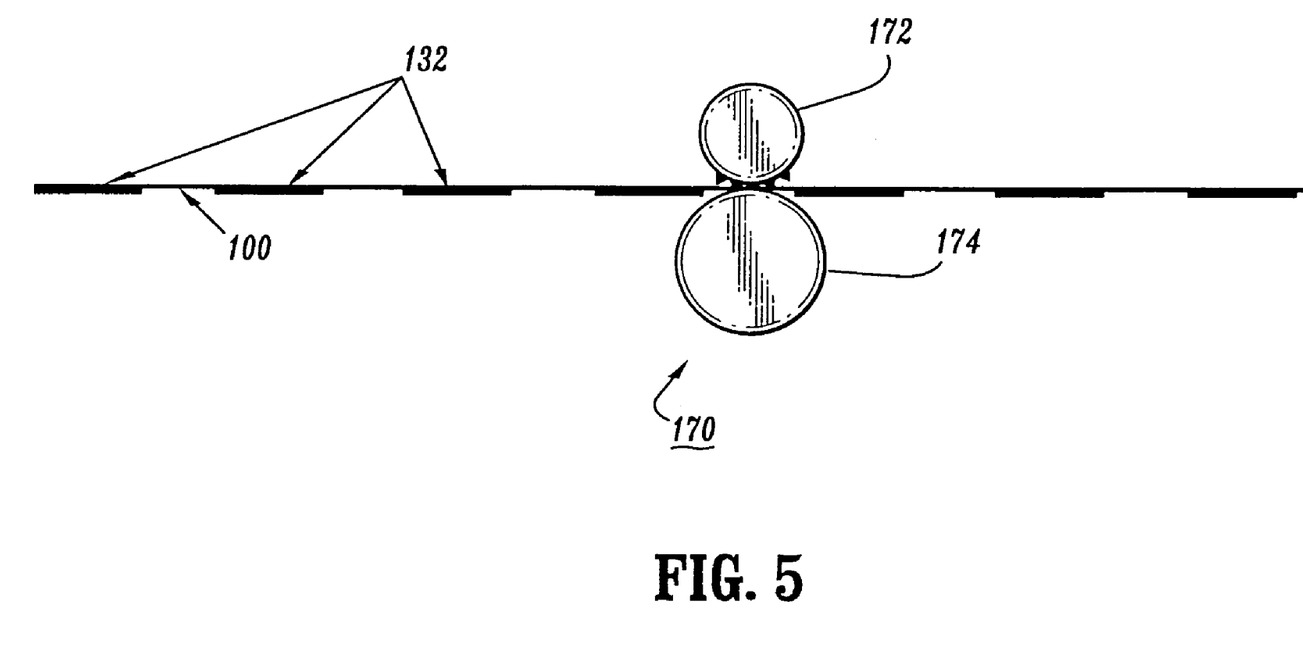
FIG. 5 is a schematic diagram of a cutting apparatus, for the method of manufacturing absorbent articles, that precuts the elastic members within first elastic region and/or second elastic region laminates.

FIG. 5 is a schematic diagram demonstrating a method for precutting the second elastic region elastic members 42 and/or the first elastic region elastic members 40 in the regions that will correspond to the distal region of the side panels 24 and/or the body facing region 20. As the laminate 100 exits the compression rollers 160 (see FIG. 3), it is next passed through the cutting rollers 170. The cutting rollers 170 typically consist of a knife roller 172 apposed against an anvil roller 174. The knife roller 172 has raised cutting edges on a portion of its circumference such that the laminate 100 is cut in the regions between the adhesive 132. In preferred embodiments, the circumference of the knife roller 172 is conveniently substantially the same length as the width of the absorbent article 10. Thus, each revolution of the knife roller 172 precuts the elastic members 110 within the laminate in the desired pattern as described, for example, in FIGS. 1 and 2. It is also contemplated that, in an alternative embodiment, multiple cutting rollers 170 may be used to obtain the desired final precut pattern. This precutting of the elastic members 110 effectively releases the elastic tension in that region of the laminate 100. The diameter of anvil roller 174 is usually, but not always, larger than that of the knife roller 172. The anvil roller 174 is substantially smooth and must be sufficient to provide an apposing surface against which the knife roller 172 can act. In another preferred embodiment, either one or both of the knife roller 172 and the anvil roller 174 are heated so that the upper sheet 152 and the lower sheet 142 are melt-sealed at each cut. This melt-sealing aids in preventing the top sheet 152 and the lower sheet 142 from separating and also aids in containing the discontinuous pieces of the elastic member 110 within the laminate 100.

Figure 6:
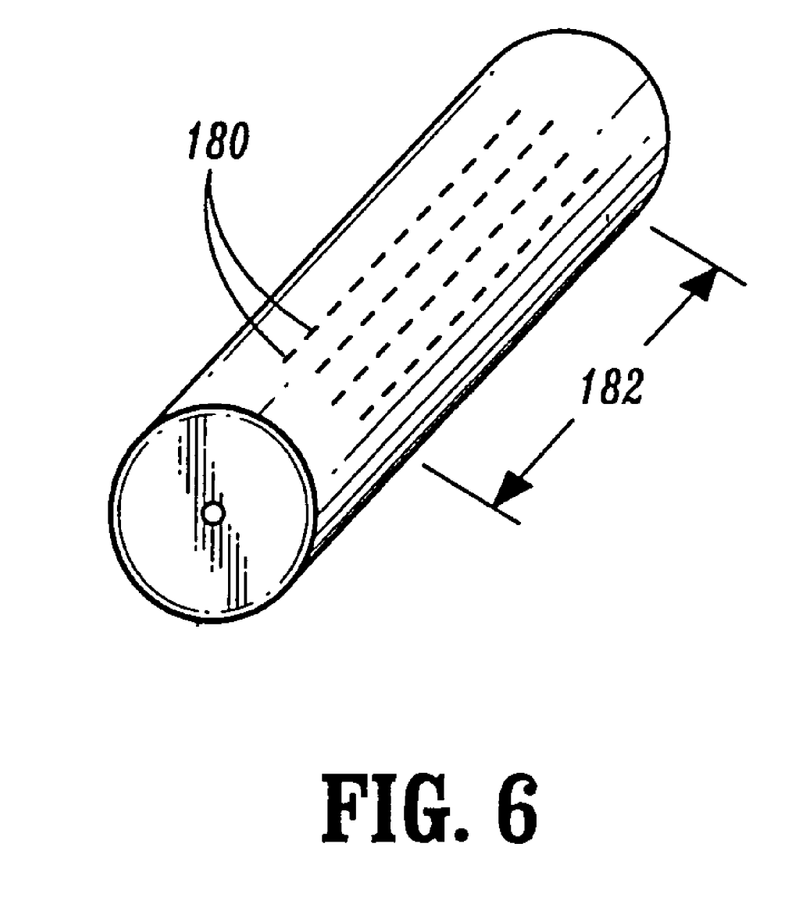
FIG. 6 is a schematic diagram of a knife roller, for the method of manufacturing absorbent articles, useful for pre-cutting the elastic members within first elastic region and/or second elastic region laminates.

FIG. 6 is a schematic diagram of a preferred embodiment of an knife roller 172. Preferably, the knife roller 172 has rows of discontinuous raised knife edges 180 and each row of raised knife edges 180 is longitudinally offset from the immediately adjacent rows. The length 182 of the rows of raised knife edges 180 is preferably greater than the width of the elastic member 110 but less than the width of the laminate 100.

Figure 7:
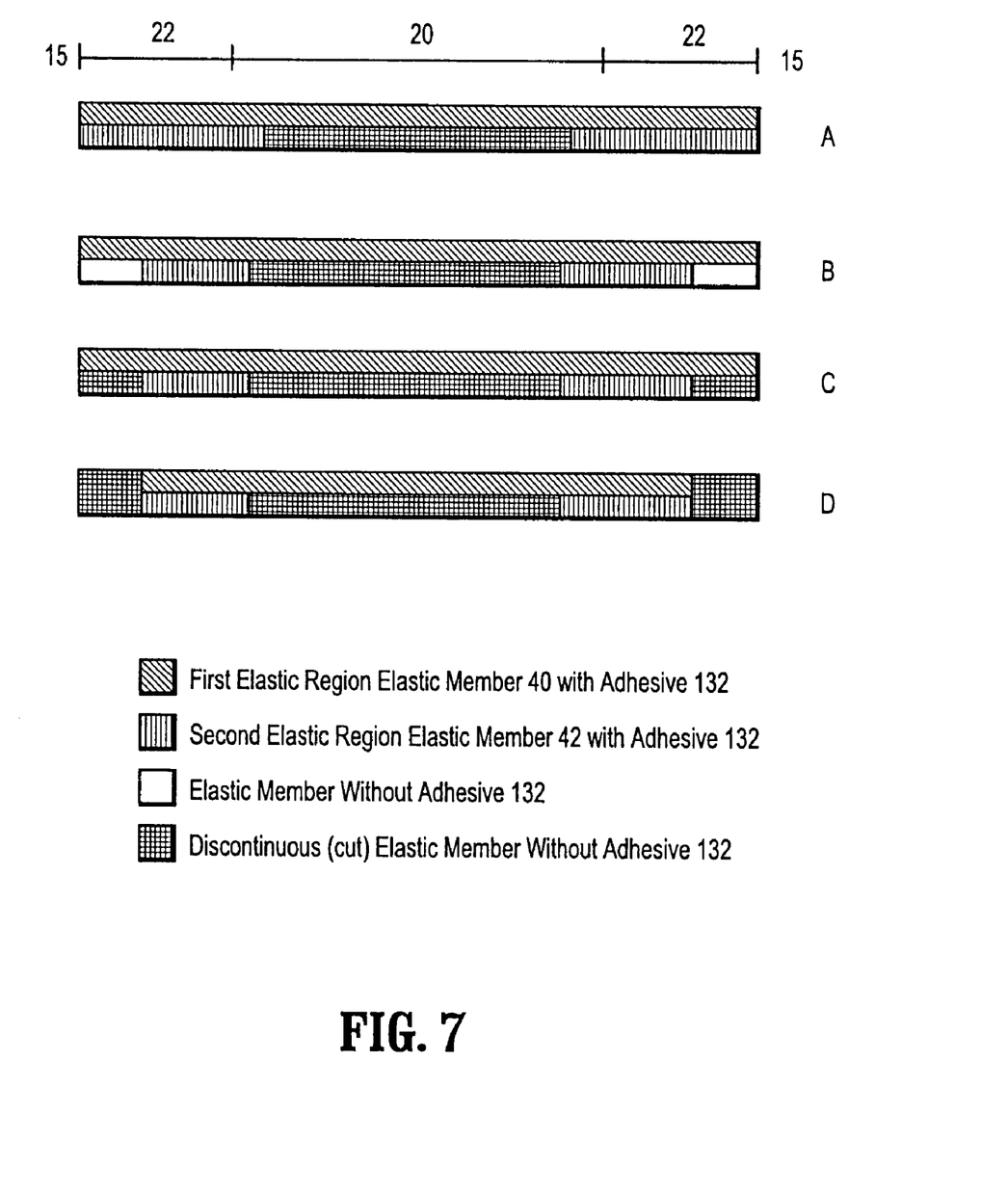
FIG. 7 is a schematic diagram showing alternative constructions of the first and second elastic regions for use in an absorbent article.

FIG. 7 is a schematic diagram showing alternate constructions combinations of first and second elastic regions for use with an absorbent article. In each case, the intact elastic members are under elastic tension. FIG. 7A shows a configuration in which the elastic tension of the elastic members of the first and second elastic regions is maintained by the use of an adhesive 132. The second elastic region band elastic member 42 is precut only in the body facing region 20. This configuration causes bunching at the side seam 15.

FIG. 7B shows an alternate configuration in which the adhesive 132 is not present on second elastic region elastic member in the side panel 22 region near the side seam 15. This configuration does not reduce or prevent side seam bunching because the second elastic region elastic member 42 remains under elastic tension because it is anchored into the side seam 15.

FIG. 7C shows one configuration made according to the principles of this disclosure. The second elastic region elastic member 42 is precut, preferably multiple times, in the side panel 22 region adjacent to the side seam 15. No adhesive is used in the precut region. This reduces the bunching problem of the prior art by relieving elastic tension adjacent to the side seam 15.

FIG. 7D shows an alternate configuration made according to the principles of this disclosure. In this configuration, both the second elastic region elastic member 42 and the first elastic region elastic member 32 are precut in the side panel 22 region adjacent to the side seam 15. Here again, no adhesive is used in the precut region. It is recognized that any elastic member may or may not be precut in the body facing region, depending upon the properties desired of the absorbent article.

Fluid permeable top sheets suitable for use with disposable absorbent articles similar to those of the present disclosure are well known in the art. The top sheet is sufficiently pervious to permit liquids (e.g., urine) to readily penetrate. Suitable top sheets may be woven or nonwoven materials, polymeric materials (e.g., apertured formed thermoplastic films, apertured plastic films, and hydroformed thermoplastic films), porous foams, reticulated foams, reticulated thermoplastic films, and thermoplastic scrims. Suitable woven and nonwoven materials include natural fibers (e.g., wood and cotton fibers), synthetic fibers (e.g., polymeric fibers such as polyester, polypropylene, and polyethylene fibers). In other embodiments, the top sheet may be treated with a surfactant to facilitate the transfer of fluid through the top sheet into the absorbent core.

Absorbent core materials and configurations for use with disposable absorbent articles similar to those of the present disclosure are also well known in the art. The absorbent core may be configured as a single continuous core or several discontinuous cores that may or may not be connected in fluid contact. The absorbent core may be symmetrical or asymmetrical and, specifically, may be configured to be gender specific. The shape of the absorbent core will depend upon the specific material used, the specific application for which the article is used, and the desired performance characteristics. The absorbent core(s) may consist of either a single type of absorbent material or may contain multiple types of absorbent materials. Suitable materials for the absorbent core include, for example, wood pulp, cellulose wadding, cotton fibers, absorbent foams, sponges, superabsorbent polymers (e.g., hydrogels), absorbent gelling materials, or combinations thereof.

Fluid impermeable back sheets for use with disposable absorbent articles similar to those of the present disclosure are also well known in the art. Preferably, the back sheet is a relatively thin (e.g., about 0.012 mm to about 0.051) plastic film. It is particularly desirable to use back sheets which, while being impervious to aqueous fluids, allows vapors to escape. Suitable material for such back sheets include, for example, microporous polyethylene and polypropylene films. In other configurations, the back sheet may be a laminate consisting of a fluid impervious film and a woven or nonwoven outer cover. There is no requirement that the outer cover be fluid impervious. Frequently the outer cover is selected for its aesthetic properties.

The disposable absorbent article of this disclosure may include structure to fasten the front and back side panels around the torso of the wearer. Such structure may include, for example, hooks, snap fasteners, and unilateral or bilateral external adhesive tabs. Alternatively, an adhesive may be applied directly to the inside face (e.g., directly on the body facing top sheet or by way of an adhesive-containing strip affixed to the top sheet) of either the front or back side panel. The adhesive is exposed by removing a protective film covering and the inner face of the adhesive-containing side panel is adhered to the outer face (back sheet) of the opposite side panel to form a side seam.

The assembly of the absorbent article may be performed according to well known principles in the art and may be varied depending upon the desired performance characteristics. For example, the absorbent cores may be "free floating" between the top sheet and back sheet, it may be adhered to the back sheet, or it may be elastically supported. The top sheet and back sheet may be joined by, for example, an adhesive or heat sealing (melting) the materials together. This process encapsulates the absorbent cores and all of the elastic members within the absorbent article to provide a unitary structure that is aesthetically appealing.

Although the foregoing disclosure has been described in some detail by way of illustration and example for purposes of clarity of understanding, it will be readily apparent to those of ordinary skill in the art in light of the teachings of this present disclosure that certain changes and modifications may be made thereto without departing from the spirit or scope of the appended claims.

What is claimed is:

1. A method for manufacturing an absorbent article comprising the steps of:
   i. providing a single elastic member, an upper sheet, a lower sheet and an adhesive;
   ii. applying said adhesive to at least one side of said single elastic member;
   iii. assembling a laminate structure wherein said single elastic member is disposed between said upper sheet and said lower sheet;
   iv. making internal cuts in said single elastic member so as to form at least one continuous elastic member and at least one discontinuous elastic member within said single elastic member;

v. assembling the absorbent article wherein said laminate structure is disposed between a body-facing surface and a garment-facing surface which are joined to form a side seam, the absorbent article comprises a front region and a back region, the at least one continuous elastic member extends continuously and without interruption across an entire width of one of the front region and the back region, and wherein said internal cuts are adjacent said side seam.

2. The method of claim 1, wherein said elastic member is under elastic tension during assembly of said laminate structure.

3. The method of claim 1, wherein said adhesive is applied discontinuously to said elastic member such that said elastic member is characterized as having adhesive-containing regions and non-adhesive-containing regions.

4. The method of claim 3, wherein said internal cuts are made in non-adhesive-containing regions of said elastic member.

5. The method of claim 1, wherein said internal cuts are made with a heated knife roller.

6. The method of claim 5, wherein said adhesive is further disposed between said elastic member and said garment-facing surface.

7. A method for manufacturing a laminate structure comprising the steps of:

i. providing a single elastic member, an upper sheet, a lower sheet, and an adhesive, the single elastic member having a first end and a second end;

ii. discontinuously applying said adhesive to at least one side of said single elastic member such that said single elastic member is characterized as having adhesive-containing regions and non-adhesive-containing regions;

iii. assembling said laminate structure wherein said single elastic member is disposed between said upper sheet and said lower sheet, and wherein said single elastic member is under elastic tension during assembly;

iv. making internal cuts in said laminate structure so as to form at least one continuous elastic member and at least one discontinuous elastic member within said single elastic member, the continuous elastic member extending continuously and without interruption from the first end to the second end of the elastic member, wherein said internal cuts are made in the non-adhesive-containing regions of said elastic member such that the elastic tension of said elastic member is relieved in the area of said internal cuts.

8. The method of claim 7, wherein said internal cuts are made with a heated knife roller.

9. The method of claim 7, wherein said upper sheet and said lower sheet are joined at the edges of said laminate structure.

\* \* \* \* \*